United States Patent [19]
Lambers et al.

[11] Patent Number: 6,147,118
[45] Date of Patent: Nov. 14, 2000

[54] ANTIMICROBIAL COMPOSITIONS FOR TOPICAL USE

[75] Inventors: Johannes Wilhelmus Jacobus Lambers, Pijnacker; Hugo Streekstra, Amsterdam, both of Netherlands

[73] Assignee: DSM N.V., Heerlen, Netherlands

[21] Appl. No.: 09/214,360

[22] PCT Filed: May 4, 1998

[86] PCT No.: PCT/EP98/02795
§ 371 Date: Dec. 29, 1998
§ 102(e) Date: Dec. 29, 1998

[87] PCT Pub. No.: WO98/49999
PCT Pub. Date: Nov. 12, 1998

[30] Foreign Application Priority Data

May 2, 1997 [NL] Netherlands ............... 97201304

[51] Int. Cl.$^7$ ................................. A61K 31/18
[52] U.S. Cl. ............... 514/603; 514/946; 514/947
[58] Field of Search ................. 514/603, 946, 514/947

[56] References Cited

U.S. PATENT DOCUMENTS

| | | | |
|---|---|---|---|
| 5,149,860 | 9/1992 | Zysman et al. | 560/160 |
| 5,578,641 | 11/1996 | Jackson et al. | 514/547 |
| 5,627,056 | 5/1997 | Casey et al. | 435/134 |
| 5,693,677 | 12/1997 | Lambers et al. | 514/844 |

FOREIGN PATENT DOCUMENTS

| | | |
|---|---|---|
| 195 03 423 | 8/1996 | Germany . |
| 196 43 585 | 4/1998 | Germany . |

OTHER PUBLICATIONS

Bibel et al., "Topical Sphingolipids in Antisepsis and Antifungal Therapy" *Clin. Exper, Dermatol.* 20:395–400 (1995).

Bibel et al., "Sphingosines: Antimicrobial Barriers of the Skin" *Acta Derm Venereol* (*Stockh*) 73:407–411 (1993).

International Search Report dated Nov. 17, 1998.

*Primary Examiner*—Kevin E. Weddington
*Attorney, Agent, or Firm*—Morrison & Foerster LLP

[57] ABSTRACT

The present invention discloses that topically occurring microbial growth is inhibited by applying a topical composition comprising a sphingoid base. Specifically, said sphingoid base is effectively formulated in combination with a surfactant.

18 Claims, 4 Drawing Sheets

ANTIMICROBIAL COMPOSITIONS FOR TOPICAL USE

FIELD OF THE INVENTION

The present invention relates to the field of topical compositions comprising sphingoid bases functioning as antimicrobial agents.

BACKGROUND OF THE INVENTION

Healthy human skin is colonized by a number of different microorganisms responsible for maintaining the natural microbial equilibrium of the skin. However, outgrowth of certain species within the skin microflora can easily occur, thereby causing cosmetically and dermatologically undesirable phenomena, like unpleasant body odour, and in a worser case, infections. Several skin conditions are known which are associated with unwanted microbial growth. For instance, wounded or diseased skin especially is prone to superinfections by *Staphylococcus aureus*, a bacterium which also is the most important infective agent in patients suffering from atopic eczema. In addition, acne is associated with outgrowth of the bacterium *Propionibacterium acnes*. Also, fungal skin infections (mycoses) are known to occur frequently.

It has been known for several decades that skin surface lipids contain one or more lipid compounds possessing antimicrobial activity against gram-positive bacteria (Burtenshaw (1942), J. Hyg. 42, 184–209). These antimicrobial lipid compounds were thought to be mainly the free fatty acids released from sebaceous triglycerides by lipases from the normal microflora (Kearney et al. (1984), Br. J. Dermatol. 110, 593–599). Only recently, attention has been focused on the role of sphingolipids in this respect.

In a recent series of papers, Bibel et al. attribute an antimicrobial activity to sphingoid bases. In a first paper, test mixtures containing about 0.0005 to 0.005% of a sphingoid base were described to inhibit in vitro microbial growth (Bibel et al. (1992), J. Invest. Dermatol. 98, 269–273). However, high concentrations of ethanol were additionally present in these mixtures and ethanol is known as a solvent which itself substantially contributes to antimicrobial activity. Furthermore, no or a very low activity against gram-negative bacteria was observed. In in vivo experiments (Bibel et al. (1992), supra; Bibel et al. (1995), Clin. Exper. Dermatol. 20, 395–400), sphingoid bases were applied in much higher concentrations, i.e. as an 1.6% ethanolic solution or as a suspension of an 1.5% ethanolic solution in petrolatum. However, these formulations are not considered to enable an effective delivery of an active ingredient to the skin. For instance, Bibel et al. (1995) reported granulation of sphinganine upon drying, resulting in a decreased availability of this compound.

The present invention discloses compositions for the inhibition of topically-occurring microbial growth which comprise an effectively formulated sphingoid base, i.e. a sphingoid base which is formulated without ethanol in a high concentration.

DESCRIPTION OF THE INVENTION

The present invention discloses that sphingoid bases have a potent antimicrobial activity in the absence of inhibiting concentrations of an antimicrobial solvent like ethanol. Effective formulations are disclosed which are suitable for topical application on various skin conditions associated with undesired microbial growth.

The present invention further discloses that the concentration of a sphingoid base necessary to obtain a substantial antimicrobial effect in vitro in the absence of inhibiting concentrations of ethanol should be at least about 0.005 wt %. When higher concentrations are used, i.e 0.01, 0.02, 0.04 or 0.08 wt %, the antimicrobial effect of a sphingoid base increases.

Throughout the invention, the terms "antimicrobial activity/effect" or "growth-inhibitory activity/effect" are used synonymously.

Microorganisms which are susceptible to the antimicrobial activity of sphingoid bases include bacteria, yeasts and fungi.

When using a concentration of at least about 0.005% of a sphingoid base, the present invention discloses that sphingoid bases also display a growth-inhibitory activity on gram-negative bacteria. In particular, the present invention discloses that sphingoid bases display a growth-inhibitory activity against gram-negative bacteria which is about similar as compared to the activity against gram-positive bacteria.

The present invention further discloses that sphingoid bases display a substantial antifungal activity. An antifungal activity is understood to include a growth-inhibitory activity on yeasts as well as on filamentous fungi.

The present invention discloses that sphingoid bases included in compositions for topical use are effectively formulated when combined with a surfactant selected from the group of ionic (anionic and/or cationic) and nonionic surfactants. Preferably, the surfactant is selected from the group of nonionic surfactants, more preferably from the group of ethoxylated-sorbitan-esters, such as Tween 80.

The topical compositions according to the invention include compositions wherein water is used as a solvent, compositions wherein an emollient (e.g. a fat or an oil) is used as a solvent and compositions where water and a fat or an oil are used (emulsions) as a solvent.

The concentration in which the sphingoid base is effectively formulated in a topical composition may range from 0.001 to 5 wt %, preferably from 0.005 to 5 wt %, more preferably from 0.01 to 2.5 wt %, most preferably from 0.02 to 1 wt %, especially preferably from 0.02 to 0.5 wt %.

It thereby may depend on the type of application which concentration of a sphingoid base advantageously is used. Typically, treatment of an infection, e.g. a wound infection, may require a higher dose of a sphingoid base than preventive use, e.g. the normalisation of skin flora.

The surfactant typically is applied in a concentration ranging from 0.01 to 10%, preferably from 0.1 to 5%, more preferably from 0.5 to 2.5%.

The type of sphingoid base used is not critical to the invention. Typically, a sphingoid base is selected from the group of sphinganines, sphingosines or phytosphingosines. Preferably, a sphingoid base is selected from the group of phytosphingosines.

The sphingoid bases used according to the invention may be obtained from any suitable source, e.g. from a natural source or from a chemical synthesis process. However, it is desirable to apply a production process such that a sphingoid base is obtainable in sufficient quantities at commercially feasible prices. In that regard, some current sources of sphingoid bases may have disadvantages. In case of chemical synthesis, it is very difficult to prepare the correct stereochemical configuration. In case of purification of animal and/or plant tissue extracts, the amounts of sphingoid bases are very small, making their isolation costly. Moreover, animal sources are believed to be unsafe due to the presence of viruses and other infectious agents, such as the agent causing BSE (mad cow's disease).

Therefore, sphingoid bases are preferably obtained from a microbial fermentation process. More preferably, they are obtained from a yeast, especially preferably from *Pichia ciferrii*. In one embodiment of the invention, the sphingoid base phytosphingosine is obtained from *Pichia ciferrii*-derived tetraacetyl-phytosphingosine (TAPS), by a suitable deacetylation reaction. The deacetylation may be chemical, e.g. by base catalyzed hydrolysis with potassium hydroxide, or enzymatical. After alkaline hydrolysis of TAPS, the resulting phytosphingosine may be purified. Such a purification can occur by any method known to a person skilled in the art. Yeast-derived phytosphingosine is human skin-identical, as it is reported to have the same stereochemical configuration as mammalian phytosphingosine, i.e. the D-D-erythro configuration.

Compositions according to the invention comprising a sphingoid base are suitable for topical application, whereby topical application is understood to comprise cosmetic and/or dermatological application on the skin, on hair and on the epithelial linings of mouth, nose, eye, urogenital tract, and the like. Topical compositions including a sphingoid base are suitable to apply for various topically occurring undesirable and/or abnormal conditions associated with microbial activity.

Topical compositions according to the invention comprising a sphingoid base also advantageously are applied in the form of a plaster, dressing, and the like.

Examples of topically occurring undesirable and/or abnormal conditions in which topical compositions comprising a sphingoid base are advantageously applied are: acne, dandruff, mouth and/or lip infections, mycoses, various other skin-infectious diseases or vaginal infections. Topical compositions comprising a sphingoid base are further advantageously applied for wound-healing, e.g. in case of burns, and for normalisation of skin flora.

Due to their antimicrobial activity, sphingoid bases additionally may function as a preservative in cosmetic and dermatological compositions, to decrease and/or substitute for existing chemical preservatives.

In the following examples, the antibacterial and antifungal activity of sphingoid bases is shown. In addition, various examples of effective formulations suitable for topical application of a sphingoid base are given.

EXPERIMENTAL

Figure 1:
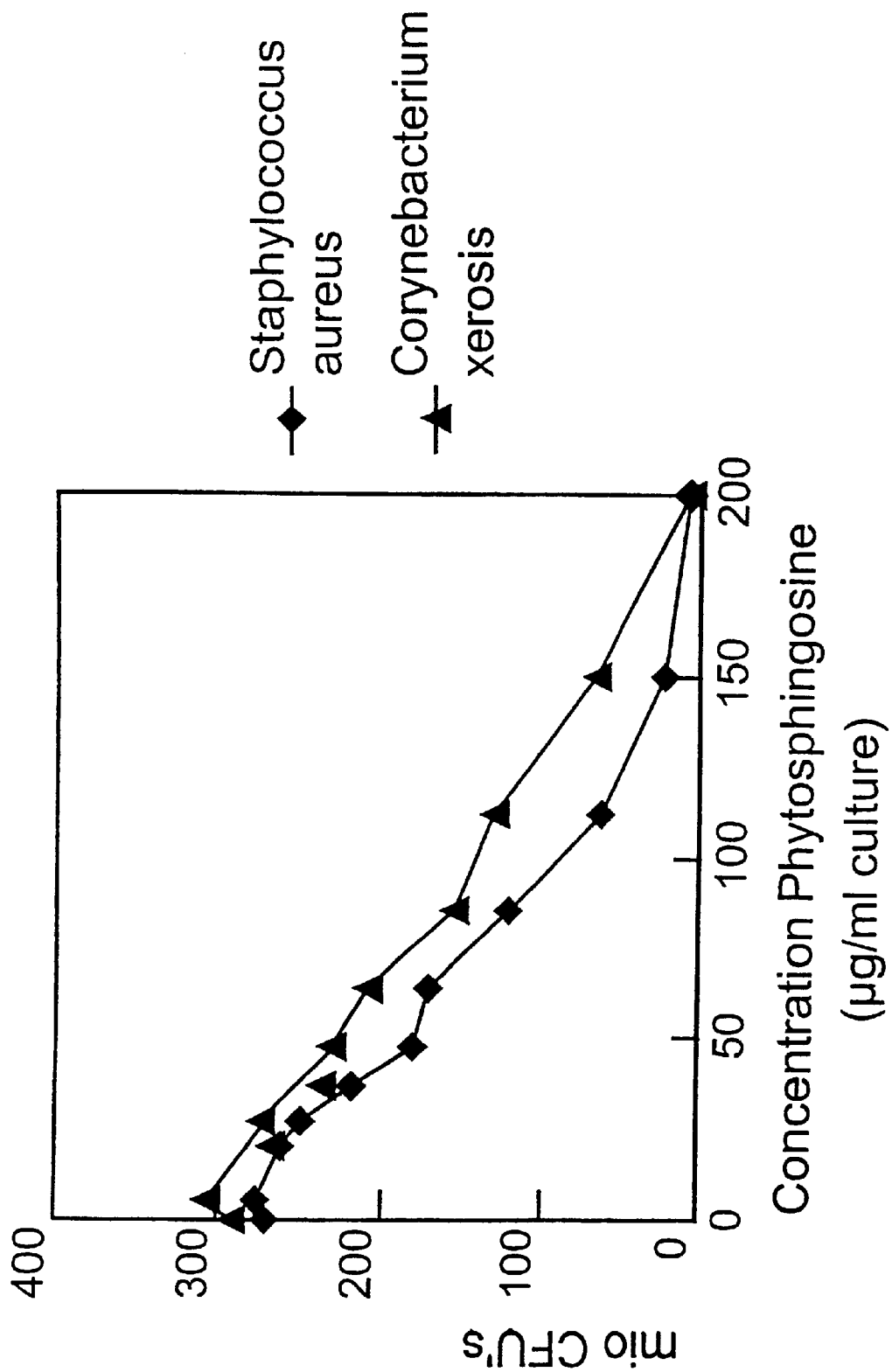
FIG. 1. CFUs obtained after incubation of *Staphylococcus aureus* and *Corynebacterium xerosis* with increasing concentrations of sphingosine.

| Strains | | |
|---|---|---|
| Gram-positive bacteria: | | |
| Micrococcus luteus | ATCC 9341 | normal flora |
| Staphylococcus aureus | ATCC 9196 | normal flora, boils |
| Corynebacterium xerosis | A 2150 | sweat |
| Propionibacterium acnes | ATCC 6919 | acne |
| Gram-negative bacteria: | | |
| Pseudomonas aeruginosa | ATCC 9027 | wound infections |
| Escherichia coli | ATCC 11229 | |
| Yeasts and fungi: | | |
| Saccharomyces cerevisiae | ATCC 9763 | |
| Candida albicans | ATCC 10231 | |
| Microsporum canis | CBS 283.63 | |

Measurement of Antibacterial Activity

All bacterial strains were grown overnight in a 500 ml shake flask containing 100 ml Brain Heart Infusion medium, at 37° C. and 280 rpm. Only *P. acnes* was grown anaerobically in BHI medium flushed with sterile nitrogen gas, for 48–72 hours at 30° C. without agitation.

The antibacterial activity of a sphingoid base of choice is measured as the amount of colony forming units (CFUs) obtained after incubation of a bacterial strain with a sphingoid base. To this end, 100 µl of a 10 times diluted overnight culture in 1% Neopeptone were added to 300 µl of a solution containing 0.7% Neopeptone, 0.6% ethanol, 1.1% Tween 80 and an appropriate amount of a sphingoid base. The resulting mixture was incubated at 37° C. during a specified time period, whereupon 100 µl of a $10^6$ times dilution in physiological salt were plated onto BHI agar plates. The resulting colonies were counted.

Measurement of Antifungal Activity

Liquid Dilution Method in 96-Wells Microtiterplates a stock solution of 10 mg of phytosphingosine/ml was prepared in water containing 20% ethanol and 16% Tween 80;

from the stock solution a ten-fold dilution was prepared in Sabouraud dextrose broth (Difco);

from *Saccharomyces cerevisiae* and *Candida albicans* cultured on Sabouraud dextrose broth several serial dilutions were prepared in said medium in a total count twice as much as is needed in the test;

100 µl of the ten-fold dilution of phytosphingosine was added to the first wells of the left side (in a vertical way) of a 96-wells microtiterplate;

to each row of wells 100 µl of the appropiate culture and dilution was added in such a way that the highest total count is on top;

after mixing the first well, 100 µl from this well was added to the second well at the right side;

after mixing the second well, 100 µl from this well was added to the third well at the right side etc.;

for each row this dilution rate was made, thus preparing from left to right a dilution rate of 1000, 500, 250 microgram of phytosphingosine/ml etc. and from top to bottom a serial dilution rate in total count;

after incubation at appropiate temperature and time, growth was measured by examining sedimentation on the bottom of the wells using a mirror;

the concentration of phytosphingosine in the first well where no growth was observed, is the value for the minimal inhibitory concentration (mic).

Agar Dilution Method a stock solution of 20 mg of phytosphingosine/ml was prepared in water containing 20% ethanol and 16% Tween 80;

from the stock solution a twenty-fold dilution was prepared in molten and cooled down Malt Extract Agar (MEA, Difco);

50 ml of this dilution was mixed with 50 ml of molten and cooled down MEA;

50 ml of the second dilution was mixed with 50 ml of molten and cooled down MEA etc, creating a dilution rate of 1000, 500, 250 μg phytosphingosine/ml MEA etc.;

from each dilution 20 ml was poured into plastic petridishes (9 cm) and cooled down to harden;

*Microsporum canis* was cultured on MEA at appropiate temperature and time;

after culturing sterile glass beads in physiological salt were added;

the culture was shaked till a homogeneous mass was obtained;

10 μl of the thus obtained cultures were spotted onto the various agardishes and cultured at appropiate temperature and time;

from cultured *Saccharomyces cerevisiae* in Sabouraud dextrose broth, appropiate serial dilutions were made in the same broth;

10 μl of the thus obtained cultures were spotted onto the various agardishes and cultured at appropiate temperature and time;

after incubation the growth was visually examined;

the concentration of phytosphingosine in the first plate where no growth was observed, is the value for the minimal inhibitory concentration (mic).

The sphingoid bases used were sphingosine (Sigma) and phytosphingosine (obtained from deacylation of *Pichia ciferri*-derived tetraacetylphytosphingosine).

EXAMPLE 1

Antibacterial Activity of Various Concentrations of Sphingosine

The antibacterial activity of sphingosine (S) on two bacterial strains was analyzed by incubating a bacterial strain with increasing concentratins of sphingosine for 60 minutes at 37° C. (see Experimental for further details).

Two representative graphs, depicting the antibacterial activity of sphingosine against *S. aureus* and *C. xerosis* (FIG. 1), show that the amount of CFUs decreases with an increasing concentration of sphingosine from 0.005 to 0.02%.

A comparable antibacterial activity of sphingosine and/or phytosphingosine was measured using *M. luteus, E. coli, P. aeruginosa* and *P. acnes*.

EXAMPLE 2

Antibacterial Activity of Phytosphingosine as Related to Time

The antibacterial activity of phytosphingosine (PS) on various bacteria as related to time was analyzed by incubating a selected bacterial strain with a solution containing phytosphingosine at 37° C. during a time period up to 240 minutes (see Experimental for further details).

Figure 2:
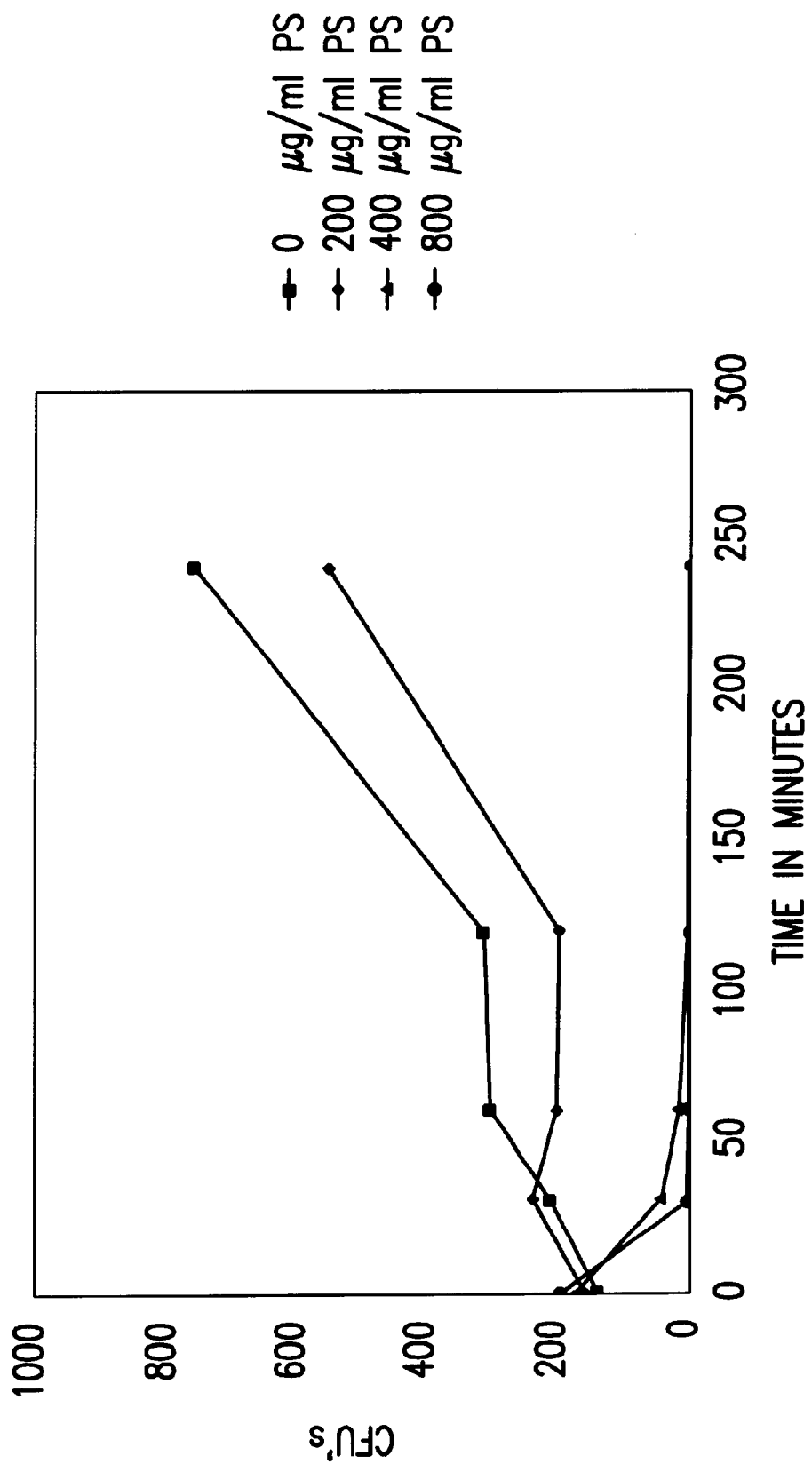
FIG. 2. CFUs obtained after incubation of *Escherichia coli* during an increasing time period with three concentrations of phytosphingosine.
Figure 3:
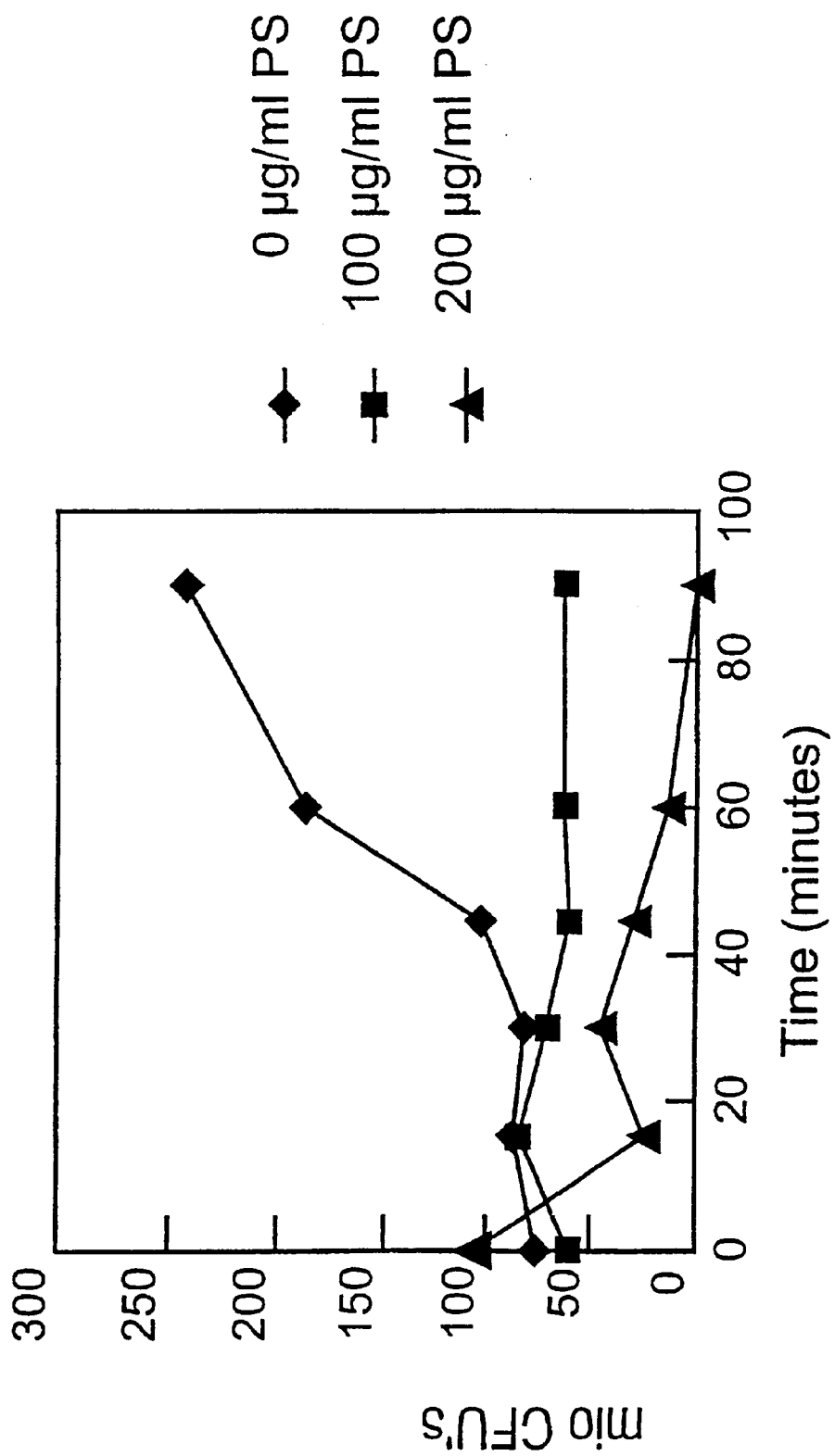
FIG. 3. CFUs after incubation of *Pseudomonas aeruginosa* during an increasing time period with two concentrations of phytosphingosine.
Figure 4:
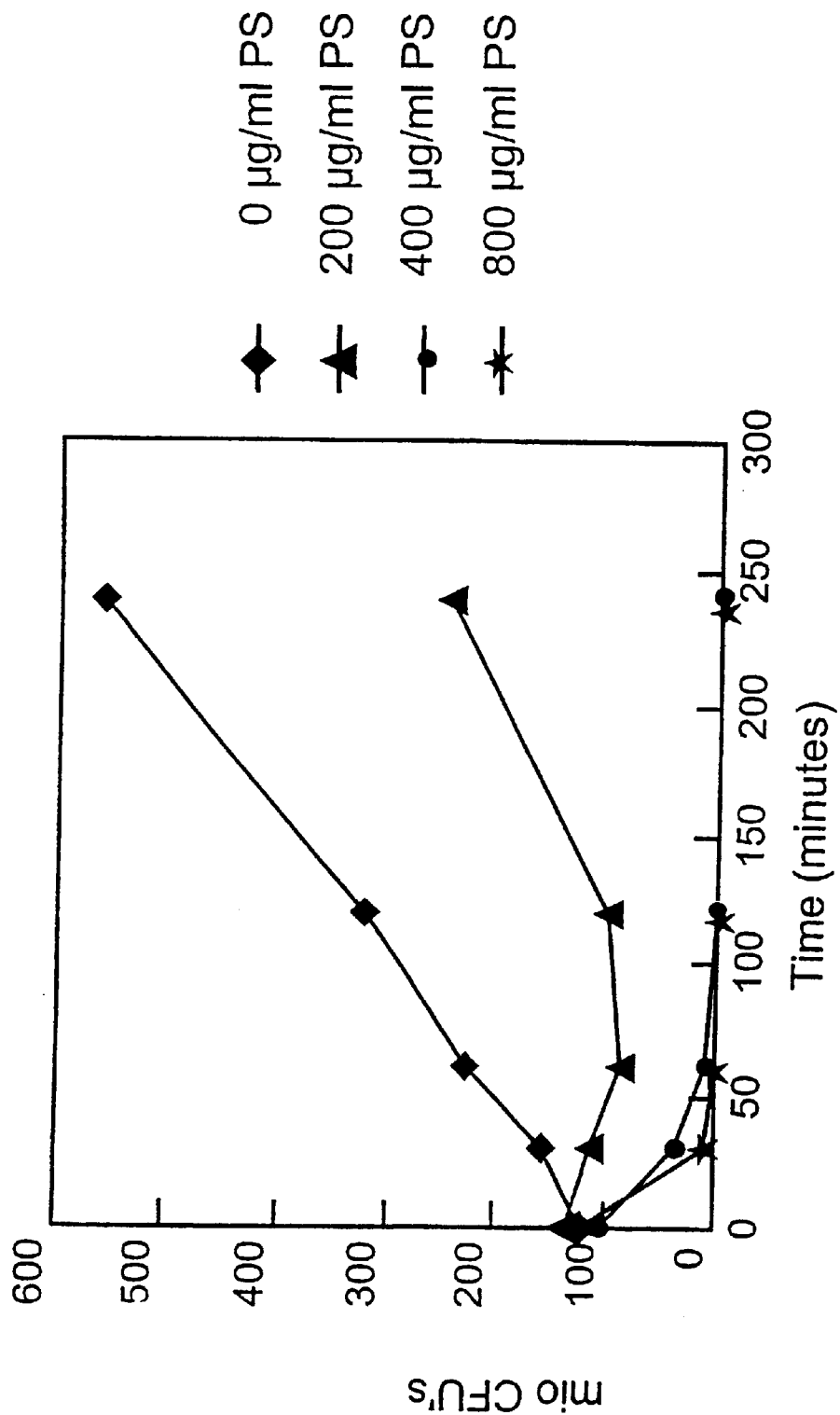
FIG. 4. CFUs after incubation of *P. acnes* during an increasing time period with three concentrations of phytosphingosine.

The results of the incubation of *E. coli, P. aeruginosa* and *P. acnes* with two or three different concentration of phytosphingosine are depicted in FIGS. 2, 3 and 4, respectively. It is shown that the outgrowth of bacteria which occurred at longer incubation times is prevented by using higher concentrations of phytosphingosine, i.e. 0.02 to 0.08 wt %.

EXAMPLE 3

Antifungal Activity of Phytosphingosine

Antifungal activity of phytosphingosine on the yeasts *S. cerevisiae* and *C. albicans* was determined using the liquid dilution method (see Experimental). The m.i.c. values obtained are indicated below. These values indicate that phytosphingosine has a potent growth inhibitory activity on yeasts.

|  | m.i.c |
| --- | --- |
| *Saccharomyces cerevisiae* | |
| $0.7 \times 10^6$ cfu/ml | 60 ppm |
| $0.7 \times 10^5$ cfu/ml | 15 ppm |
| $0.7 \times 10^4$ cfu/ml | 15–30 ppm |
| $0.7 \times 10^3$ cfu/ml | 4–8 ppm |
| $0.7 \times 10^2$ cfu/ml | 2–8 ppm |
| *Candida albicans* | |
| $0.9 \times 10^6$ cfu/ml | 125–500 ppm |
| $0.9 \times 10^5$ cfu/ml | 60–125 ppm |
| $0.9 \times 10^4$ cfu/ml | 125–250 ppm |
| $0.9 \times 10^3$ cfu/ml | 15–60 ppm |
| $0.9 \times 10^2$ cfu/ml | 125 ppm |

Antifungal activity of phytosphingosine was also determined using a dermatophyt (*M. canis*). This was done using the agar dilution method (see Experimental). For comparison, *S. cerevisiae* was also included. The results are indicated in the table below. It is clear that phytosphingosine also is able to significantly inhibit the growth of a fungus considered to be a representative of a skin fungus.

| concentration ppm | *Sacch. cerevisiae* $10^3$ cfu/ml | *Microsporum canis* |
| --- | --- | --- |
| 1,000 | –/– | –/– |
| 500 | –/– | pp/– |
| 250 | –/– | –/– |
| 125 | –/– | –/– |
| 60 | –/– | –/pp |
| 30 | –/– | +/+ |
| 15 | +++/+++ | +/+ |
| 7.5 | +++/+++ | +/+ |
| 0 | +++/+++ | +++/+++ |

+++ = good growth, ++ = moderate growth, + = very moderate growth, pp = pin point colony, – = no growth

EXAMPLE 4

Compositions Comprising a Non-Ionic Surfactant

| Standardized solution | |
| --- | --- |
| Non-ionic surfactant | 1–15% |
| Phytosphyngosine | 0.1–2% |

| -continued | |
|---|---|
| Humectant | 5–10% |
| Water | qs 100 |
| Anti acne skin cleansing lotion | |
| A. PPG-26-buteth-26 + PEG40 hydrogenated castor oil | 1% |
| Phytosphyngosine | 0.2% |
| Butylene glycol | 5% |
| B. Water | qs 100 |

Procedure: Combine all ingredients of A by mixing. Add B to A while stirring and keep on stirring until the product is homogeneous.

| Antimicrobial mouthwash concentrate | |
|---|---|
| A. Glycerin | 20% |
| Phytosphyngosine | 0.1% |
| Polysorbate 80 | 1% |
| B. Flavor | 1.5% |
| Sodium Saccharin | 0.03% |
| Water | qs 100 |

Procedure: Dissolve phytosphingosine into the polysorbate at room temperature, add the glycerin. Then add B to A and mix until homogeneous.

EXAMPLE 5

Oil/Water Emulsions

| Standardized emulsion | |
|---|---|
| A. various oil phase | 10–25% |
| non-ionic surfactants | 2–7% |
| B. humectant | 5–10% |
| non-ionic surfactant | 1–4% |
| phytosphingosine | 0.1–1% |
| water | qs 100 |
| Therapeutic Foot cream | |
| A. Water | 70% |
| B. Mineral oil | 5% |
| C12–C15 alcohol benzoate | 2% |
| Propylene glycol dicapralate | 5% |
| Dimethicone | 1% |
| Ceteareth 21 | 3% |
| Ceteareth 2 | 2% |
| C. Propylene glycol | 10% |
| Ethoxylated hydrogenated castor oil | 1% |
| Phytosphyngosine | 0.2% |
| D. Perfume | qs |

Procedure: Heat A and B to 75–80° C. and mix for 30 minutes with good agitation. Cool to 40° C. add C and D.

EXAMPLE 6

Cleansing Compositions

| Standardized soap solution | |
|---|---|
| Anionic surfactant | 0–15% |
| Amphoteric surfactant | 0–15% |

| -continued | |
|---|---|
| Non-ionic surfactant | 0–20% |
| Phytosphingosine | 0.1–1% |
| EDTA | 0.05% |
| Water | qs 100 |
| Anti-microbial facial cleanser | |
| A. Sodium laureth sulfate | 12% |
| Cocamidopropylbetaine | 3% |
| Cocamide DEA | 2% |
| Phytosphingosine | 0.1% |
| B. Propylene glycol | 20% |
| Water | qs 100 |
| Fragrance | qs |

Procedure: Combine A and B at 40° C. When homogeneous add C under stirring.

| Skin Lotion with phytosphyngosine | |
|---|---|
| A. Water | 70% |
| Carbomer | 0.3% |
| B. Mineral oil | 5% |
| C12–C15 alcool benzoate | 2% |
| Propylene glycol dicapralate | 5% |
| Cetyl alcohol | 1% |
| Stearic acid | 3% |
| C. Dimethicone | 1% |
| D. Butylene glycol | 7% |
| Oleic acid | 1% |
| Phytosphingosine | 0.2% |
| E. Triethanolamine | 1% |
| Water | qs 100 |
| F. Perfume | qs |

Procedure: Disperse A. Heat B to 75–80° C. and mix until uniform. Combine with A and mix for 30 minutes with good agitation. Cool to 60° C. and add C. Cool to 40° C. add D, E and F.

EXAMPLE 7

Gel Composition

| Standardized gel formulation | |
|---|---|
| Gellifiant | 0.5–3% |
| Humectant | 5–50% |
| Phytosphingosine | 0.1–2% |
| Water | qs 100 |
| Anti acne gel | |
| A. Natrosol | 2, 25% |
| Water | qs 100 |
| B. Ethoxydiglycol | 20% |
| Phytosphingosine | 0.2% |

Procedure: Disperse the Carbomer into the water, then add B. Adjust the pH with triethylamine (TEA).

| Roll on deodorant | |
|---|---|
| A. Propylene glycol | 30% |
| Phytosphingosine | 0.1% |

-continued

| Roll on deodorant | | |
|---|---|---|
| B. Natrosol | 1.25% | |
| EDTA | 0.025% | |
| Water | qs 100 | |

Procedure: Disperse the Natrosol into the water, then add A.

What is claimed is:

1. A method for inhibiting topical microbial growth on human skin comprising the step of contacting said skin with a composition that comprises a sphingoid base and a surfactant, wherein the sphingoid base ranges from 0.001 to 5 wt % and the sphingoid base is formulated without ethanol in high concentration.

2. The method of claim 1, wherein the topical composition comprises a surfactant selected from the group of nonionic surfactants.

3. The method of claim 1, wherein said microbial growth is caused by a microorganism selected from the group of bacteria, yeasts and fungi.

4. The method of claim 3, wherein the bacteria are gram-negative bacteria.

5. The method of claim 1, wherein the topical composition comprises a sphingoid base in a concentration ranging from 0.005 to 5 wt %.

6. The method of claim 1, wherein the sphingoid base is selected from the group of sphinganines, sphingosines and phytosphingosines.

7. The method of claim 6, wherein the sphingoid base is phytosphingosine.

8. A method for inhibiting topically occurring microbial growth on human skin comprising application of a topical composition comprising a sphingoid base and a surfactant selected from the group consisting of nonionic and ionic surfactants, wherein the sphingoid base ranges from 0.001 to 5 wt % and the sphingoid base is formulated without ethanol in high concentration.

9. The method of claim 8, wherein the topical composition comprises a sphingoid base in a concentration ranging from 0.005 to 5 wt %.

10. The method of claim 8, wherein the sphingoid base is selected from the group of sphinganines, sphingosines and phytosphingosines.

11. The method of claim 8, wherein the sphingoid base is phytosphingosine.

12. The method of claim 8, wherein the topical composition is a cosmetic composition.

13. The method of claim 5, wherein the topical composition comprises a sphingoid base in a concentration ranging from 0.01 to 2.5 wt %.

14. The method of claim 13, wherein the topical composition comprises a sphingoid base in a concentration ranging from 0.02 to 1 wt %.

15. The method of claim 14, wherein the topical composition comprises a sphingoid base in a concentration ranging from 0.02 to 0.05 wt %.

16. The method of claim 9, wherein the topical composition comprises a sphingoid base in a concentration ranging from 0.01 to 2.5 wt %.

17. The method of claim 16, wherein the topical composition comprises a sphingoid base in a concentration ranging from 0.02 to 1 wt %.

18. The method of claim 17, wherein the topical composition comprises a sphingoid base in a concentration ranging from 0.02 to 0.05 wt %.

* * * * *